US009044559B2

(12) United States Patent
Grasmuck

(10) Patent No.: US 9,044,559 B2
(45) Date of Patent: Jun. 2, 2015

(54) APPARATUS FOR THE REGULATED SUPPLY OF A GAS, IN PARTICULAR AN ASSISTED BREATHING APPARATUS

(75) Inventor: Gilbert Grasmuck, La Salvetat Saint Gilles (FR)

(73) Assignee: AIR LIQUIDE MEDICAL SYSTEMS S.A., Antony (FR)

( * ) Notice: Subject to any disclaimer, the term of this patent is extended or adjusted under 35 U.S.C. 154(b) by 546 days.

(21) Appl. No.: 13/395,474

(22) PCT Filed: Nov. 29, 2010

(86) PCT No.: PCT/FR2010/052551
§ 371 (c)(1),
(2), (4) Date: Mar. 12, 2012

(87) PCT Pub. No.: WO2011/067522
PCT Pub. Date: Jun. 9, 2011

(65) Prior Publication Data
US 2012/0171058 A1 Jul. 5, 2012

(30) Foreign Application Priority Data
Dec. 2, 2009 (FR) ...................................... 09 05819

(51) Int. Cl.
*A61M 16/00* (2006.01)
*F04D 29/66* (2006.01)
*F04D 25/08* (2006.01)

(52) U.S. Cl.
CPC .......... *A61M 16/0066* (2013.01); *F04D 29/665* (2013.01); *A61M 2205/3606* (2013.01); *A61M 2205/362* (2013.01); *A61M 2205/42* (2013.01); *F04D 25/082* (2013.01); *F04D 29/664* (2013.01)

(58) Field of Classification Search
CPC ... F04D 25/082; F04D 25/12; F04D 25/0606; F04D 29/663; F04D 29/664; F04D 29/665; A61M 16/0057; A61M 16/0066; A61M 2202/0208; A61M 2205/3368; A61M 2206/42

USPC ............ 417/366, 423.8, 423.14; 128/200.24, 128/204.18, 204.21, 205.18; 415/119, 206, 415/214.1

See application file for complete search history.

(56) References Cited

U.S. PATENT DOCUMENTS 6,837,260 B1 * 1/2005 Kuehn ..................... 137/315.01
7,617,823 B2 * 11/2009 DiMatteo et al. ........ 128/204.18
(Continued)

FOREIGN PATENT DOCUMENTS

| FR | 2843305 | 2/2004 |
|----|---------|--------|
| FR | 2908482 | 5/2008 |
| FR | 2910081 | 6/2008 |
| WO | 99/22793 | 5/1999 |

(Continued)

OTHER PUBLICATIONS
International Search Report dated Apr. 4, 2011, in corresponding PCT application.

*Primary Examiner* — Devon Kramer
*Assistant Examiner* — Patrick Hamo
(74) *Attorney, Agent, or Firm* — Young & Thompson

(57) ABSTRACT

An apparatus for supplying gas, includes a ventilator having a motor, a rotor having vanes and a volute, a conduit for cooling the motor, and a soundproofing housing containing the ventilator and the conduit. The conduit has a shape similar to the wall of the motor and the volute, thus providing a flow path around the motor and the volute. The conduit also includes two housing portions, one of which includes a set of walls, forming a portion of the soundproofing housing and the conduit, and the other also includes a set of walls, forming the matching portion of the soundproofing housing and the conduit. The portions of the soundproofing housing and the conduit on the same portion of the housing are integral with one another, the two portions being suitable for being assembled together around the ventilator such as jointly to form the conduit and the soundproofing housing.

14 Claims, 4 Drawing Sheets

(56) References Cited

U.S. PATENT DOCUMENTS

2008/0304986 A1* 12/2008 Kenyon et al. ........... 417/423.12
2010/0054969 A1* 3/2010 Grasmuck ................... 417/371

FOREIGN PATENT DOCUMENTS

| WO | 2007/024955 | 3/2007 |
| WO | 2008/131202 | 10/2008 |

* cited by examiner

APPARATUS FOR THE REGULATED SUPPLY OF A GAS, IN PARTICULAR AN ASSISTED BREATHING APPARATUS

The present invention relates to an apparatus for the regulated supply of a gas, especially an assisted breathing apparatus.

It is known to use an apparatus for the regulated supply of a gas, especially an assisted breathing apparatus, comprising a fan essentially consisting of a motor, a vaned rotor and a volute containing this rotor, a duct for cooling the motor of the fan, and a soundproofing housing containing the fan and the motor-cooling duct, as for example described by the document FR-A-2908482.

The type of fan motor used and the rapid rotation of this motor cause the motor to heat up substantially, and it is a critical to cool this motor. Specifically, effective cooling of this motor has a direct impact on the performance and the longevity of the apparatus.

Now, existing apparatuses are not perfectly satisfactory from this standpoint.

In addition, the existing apparatuses have relatively complicated structures involving a large number of parts, assembly difficulties and a long assembly time.

Furthermore, in this type of apparatus, the design of an air inlet for obtaining both a low sound level and a minimized pressure drop is difficult.

The aim of the present invention is to remedy all these drawbacks, that is to say in particular to propose an apparatus for supplying a gas such as an assisted breathing apparatus, in which sufficient and effective cooling of the motor is provided, said apparatus furthermore having a simple architecture that does not complicate its assembly.

Preferably in a regulated manner, the solution according to the present invention is an apparatus for delivering a gas, in particular an assisted breathing apparatus, comprising a fan comprising a motor, a vaned rotor and a volute containing this rotor, a duct for cooling the motor, and a soundproofing housing containing the fan and the motor-cooling duct, characterized in that:

the motor-cooling duct has a shape matched to the shape of the motor and that of the volute of the fan, so that the walls defining this motor-cooling duct extend close to the wall of the motor and the volute, thus providing a flowing duct around this motor and this volute; and the apparatus comprises two casing portions, one of which includes a set of walls, comprising a back wall and at least one side wall, forming a portion of the soundproofing housing and a set of walls forming a portion of the motor-cooling duct, and the other of which includes a set of walls comprising a back wall and at least one side wall, forming the complementary portion of the soundproofing housing, and a set of walls forming the complementary portion of the motor-cooling duct, said portions of the soundproofing housing and of the motor-cooling duct on the same casing portion being integral with one another, and the two casing portions being able to be assembled together around the fan so as jointly to form said motor-cooling duct and said soundproofing housing.

The apparatus according to the invention thus includes a motor-cooling duct, forcing the liquid, that is to say the gas, driven by the vaned rotor, to flow in the immediate proximity of the external walls of the motor and of the volute, and therefore ensuring effective cooling of these components, while still having this motor-cooling duct formed as one and the same piece with the soundproofing housing, thus making it possible, by forced convection, to discharge the heat generated by the motor. Optimum cooling of the fan motor is thus obtained.

Assembly of the apparatus is made possible by the design of the motor-cooling duct and of the soundproofing housing in the form of the two aforementioned casing portions. This design, apart from the performance obtained in terms of cooling the motor, also has the following advantages: the number of parts making the apparatus is appreciably reduced; it results in greater ease of assembly, and therefore a shorter assembly time; and less material is needed to make the motor-cooling duct and the soundproofing housing.

Furthermore, the casing portions may be provided by molding, thereby increasing the possibility of positioning the motor-cooling duct in the soundproofing housing and of optimally integrating into the apparatus a fluid inlet having a high acoustic attenuation and a minimized pressure drop.

Preferably, the casing portions are half-casings that can be assembled together in an assembly plane passing substantially through the longitudinal axis of the motor-cooling duct, that is to say the axis with which the rotation axis of the vaned rotor of the fan coincides when the fan is in the mounted position in said motor-cooling duct.

According to another possibility, the casing portions can be assembled together in an assembly plane substantially perpendicular to the longitudinal axis of the motor-cooling duct, that is to say the axis with which the rotation axis of the vaned rotor of the fan is coincident when the fan is in the mounted position in said motor-cooling duct.

The fitting of the fan in a first half-casing is thus facilitated, as is the assembly of the second half-casing with the first half-casing.

Preferably, each casing portion forms at least one housing portion, and the two housing portions jointly form, after assembly of the casing portions, a housing suitable for closely accommodating a corresponding portion of the fan, either directly or with interposition of a mounting element, especially a soft vibration-damping element.

Thus, not only is it easier to mount the fan in the motor-cooling duct, but also, and above all, it is mounted with perfect damping of the vibrations generated by the fan.

Each casing portion may especially comprise a lower housing portion, and the two lower housing portions jointly form, after assembly of the casing portions, a housing capable of closely accommodating the opposite end of the motor from the volute or a piece fixed at this end.

Thus, said end of the motor is perfectly immobilized in a simple manner. Said housing may especially be provided in the side wall of the casing close to the lower end of the motor-cooling duct.

Each casing portion may also comprise a portion for housing the outlet nozzle of the volute, the two portions for housing the outlet nozzle of the volute jointly forming, after assembly of the casing portions, a housing capable of closely accommodating the outlet nozzle of the volute, with interposition of a mounting/damping seal.

Each casing portion may also comprise a housing portion for fitting the fan, the two housing portions for fitting the fan jointly forming, after assembly of the casing portions, a housing capable of closely accommodating a stud for fitting the fan, integral with the volute, with interposition of a mounting/damping seal.

Each housing portion for fitting the fan may especially be provided at a location in the motor-cooling duct diametrically opposed to the portion for housing the outlet nozzle of the volute.

The two casing portions may be assembled by any means, especially by screwing them together or by bonding them.

Depending on the case, the apparatus of the invention may also include one or more of the following features:

- it comprises two casing portions one of which includes a set of walls comprising a back wall and several side walls forming a portion of the soundproofing housing and a set of walls forming a portion of the motor-cooling duct, and the other of which includes a set of walls comprising a back wall and several side walls; the two casing portions preferably comprise four side walls
- the casing portions are provided by molding;
- the motor-cooling duct is formed as one and the same piece with the soundproofing housing;
- the motor-cooling duct has a fitted shape approximately matching the shape of the motor and of the volute of the fan, while providing a space around the motor and the volute within which a gas may flow;
- the two housing portions jointly form, after assembly of the casing portions, a housing suitable for closely accommodating a corresponding portion of the fan with interposition of a soft vibration-damping element;
- the internal wall of the motor-cooling duct has a shape that matches the external contour of the motor and of the volute of the fan, while being spaced apart from the external surface of said contour of the motor and of the volute so as to form between them a passage for the gas, that is to say a spacing capable of allowing gas in contact with the external surface of the motor, to flow, and therefore to cool the said motor; and
- the two casing portions are fastened together around the fan, in particular by screwing, especially by means of screws, bolts, nuts or any other similar fastening means.

The features and the operation of the apparatus for the regulated supply of a gas according to the invention will be better understood by virtue of the following detailed description given with reference to the appended figures in which.

Figure 1:
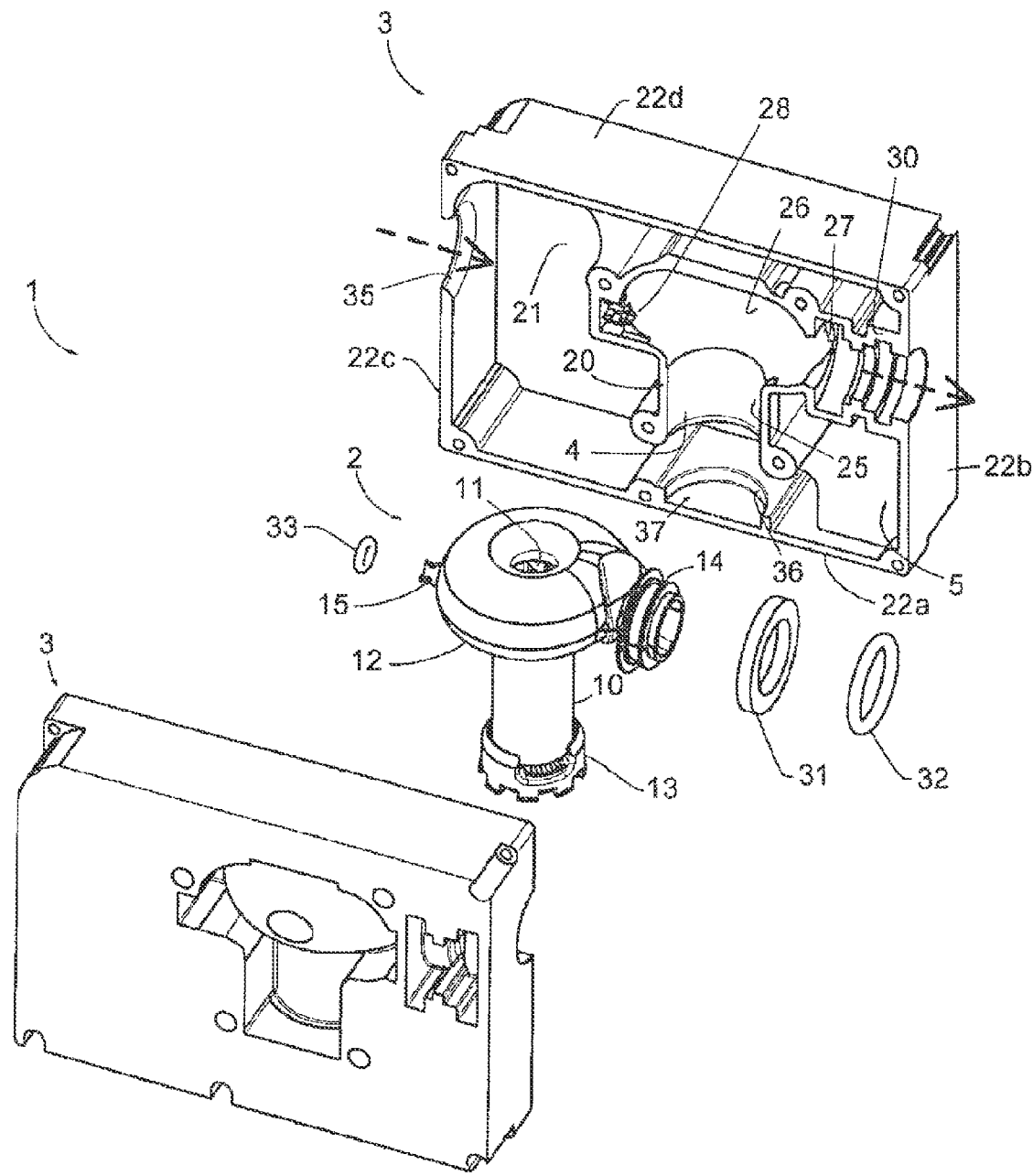
FIG. 1 is a view of the apparatus of the invention in exploded perspective.
Figure 2:
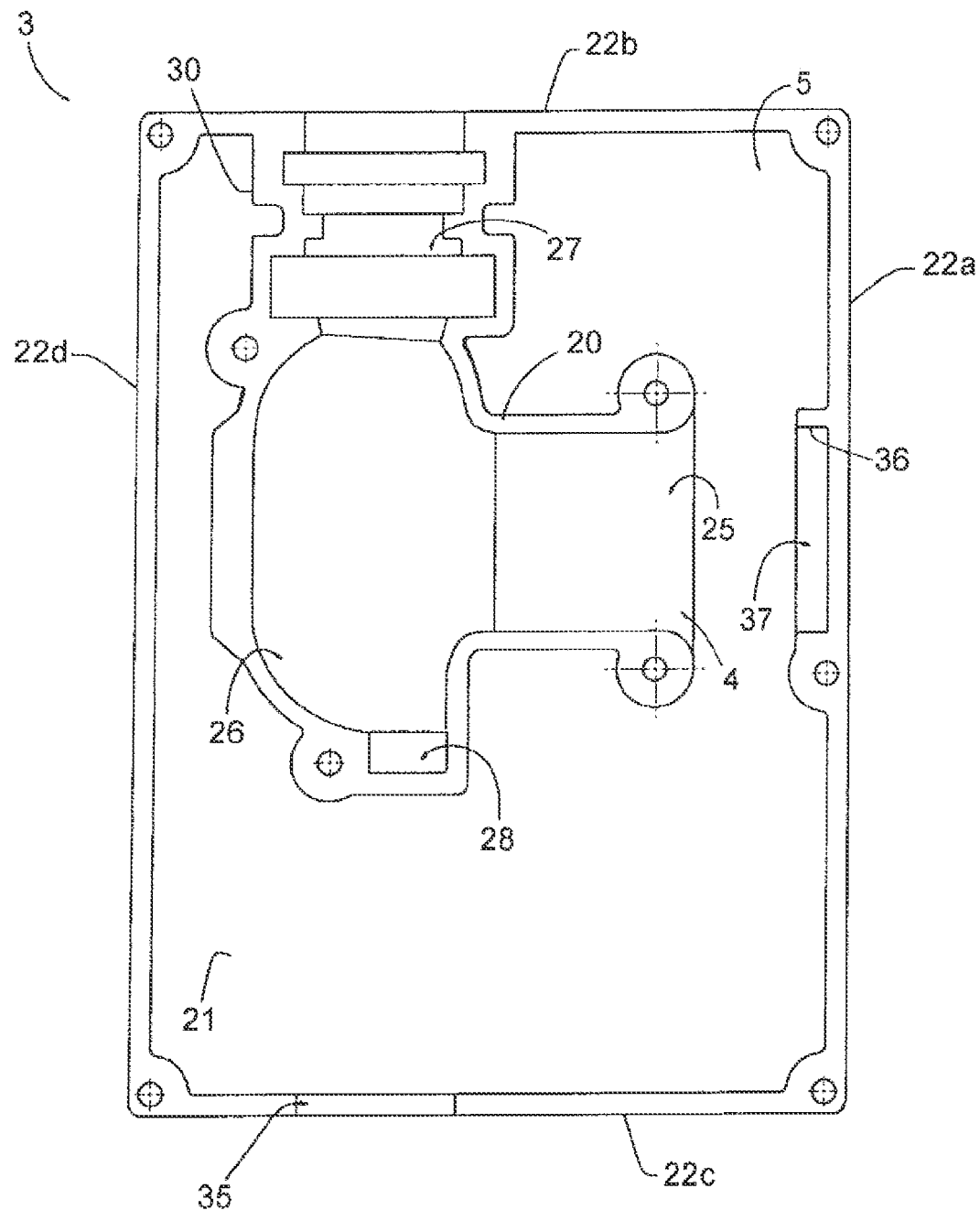
FIG. 2 is a view of a half-casing of this apparatus, before a fan is fitted into the apparatus.
Figure 3:
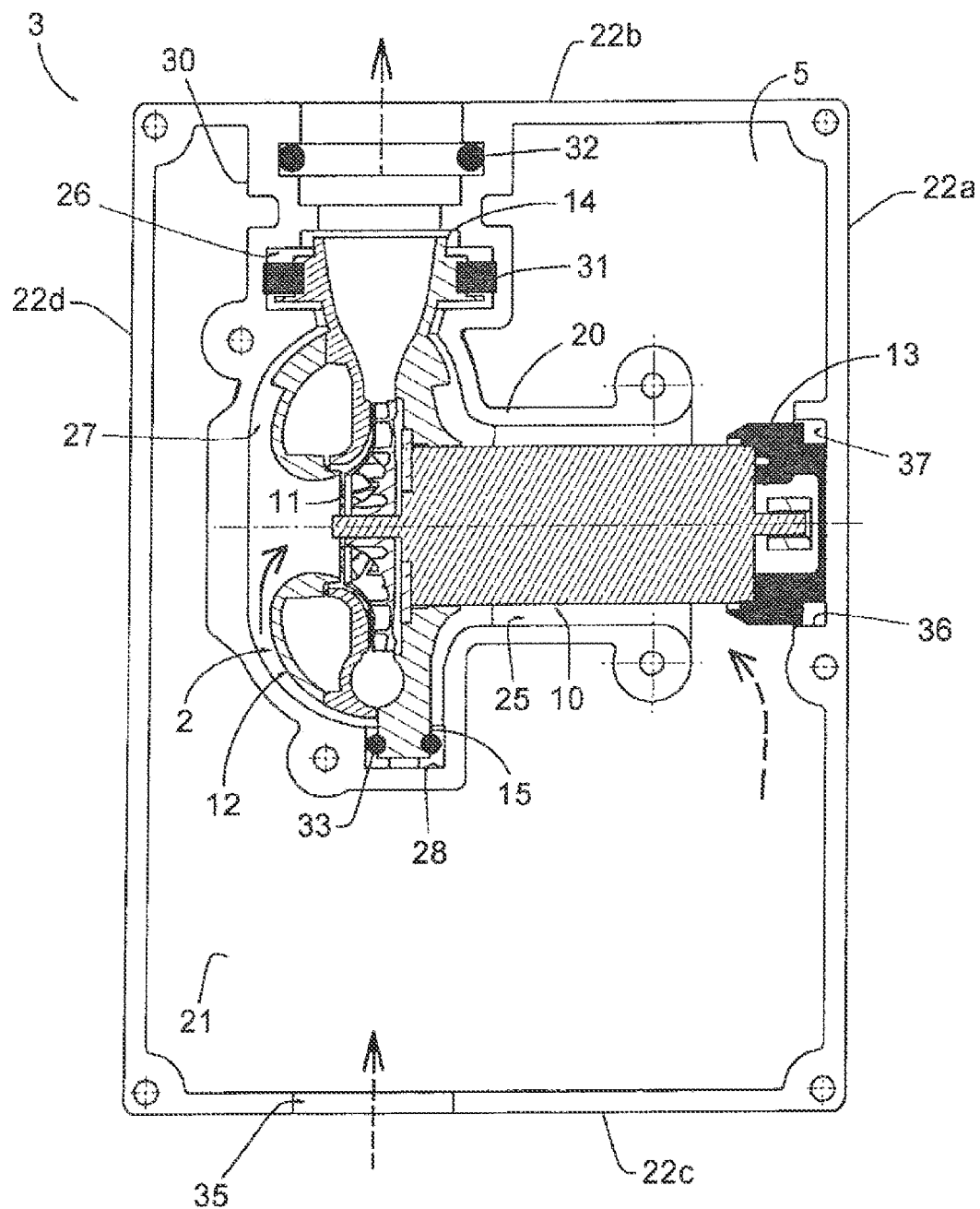
FIG. 3 is a view of the half-casing similar to FIG. 2, after the fan has been fitted.
Figure 4:
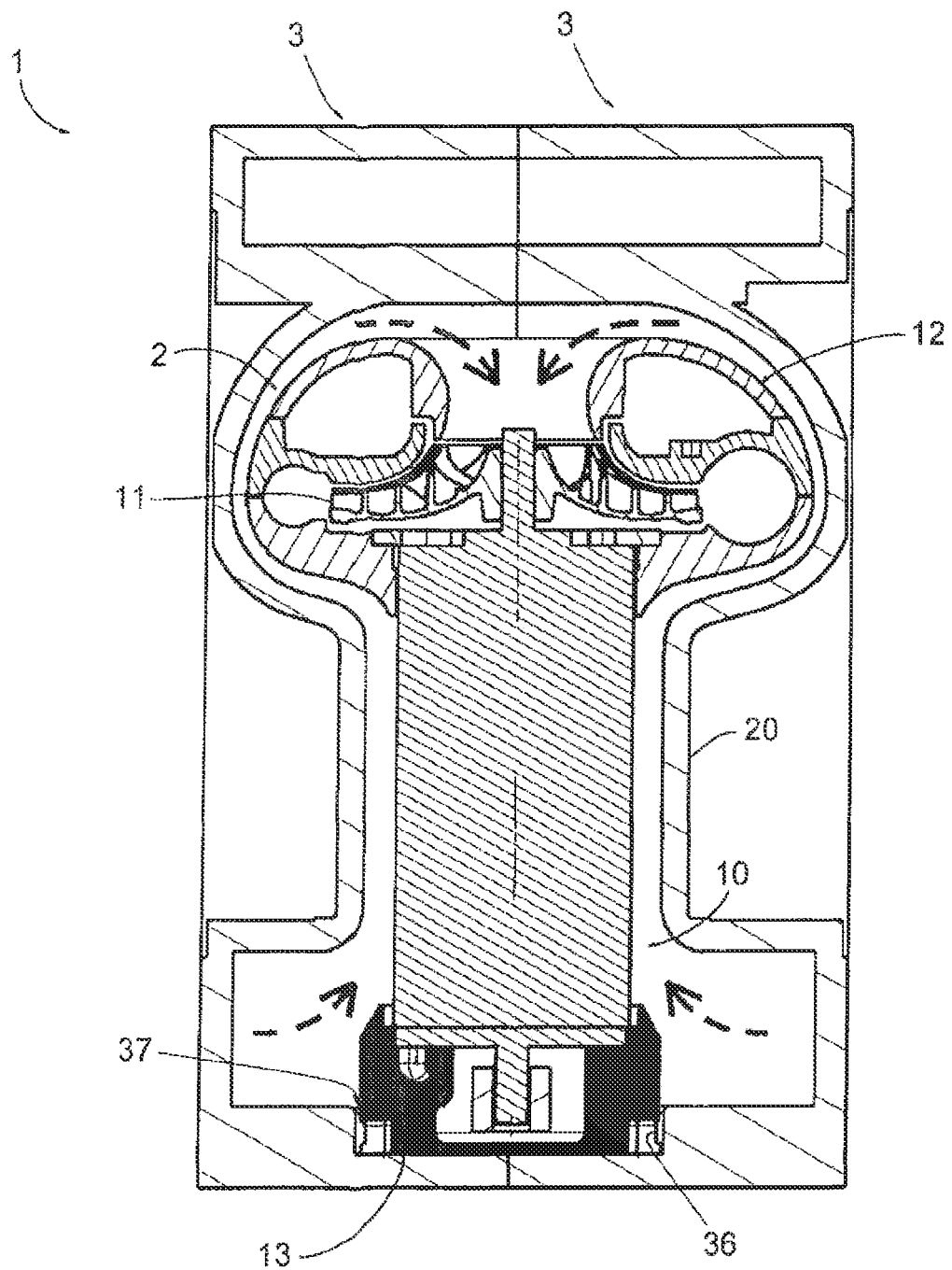
FIG. 4 is a cross-sectional view of the apparatus passing through the rotation axis of a vaned rotor that the fan includes.

FIGS. 1 to 4 show an apparatus 1 for the regulated supply of a gas, especially an assisted breathing apparatus, comprising a fan 2 and two half-casings 3 that can be assembled together around this fan 2, the assembly of these half-casings 3 making it possible to form a duct 4 for cooling the motor of the fan 2, and a soundproofing housing 5.

In these figures, the broken-line arrows depict the flow of the gas, that is to say the flow of air.

The fan 2 essentially consists of a motor 10, a vaned rotor 11 and a volute 12 containing this rotor 11. The motor 10 has a cylindrical general shape and includes an axial shaft on which the rotor 11 is mounted. In its lower portion, the fan receives, fitted onto it, an elastomeric seal 13. The vaned rotor 11 has an axial air inlet, placed in the inlet of the volute 12, air flow ducts bounded by the vanes and an upper flange thereof, and peripheral outlets. The volute 12 comprises an axial air inlet, an annular body and an air outlet nozzle 14. The combination of the above components is well known per se and will therefore not be described in greater detail.

The fan 2 also includes a stud 15 for fitting the fan 2 with respect to the duct 4, which is integral with the volute 12. This stud 15 has a substantially cylindrical shape and extends radially outwards from the volute 12, being located at a diametrically opposite position with respect to the nozzle 14.

Each half-casing 3 is formed from a single piece molded from a plastic and comprises a series of screw holes for assembling it with the other half-casing. It comprises a set of walls 20 forming one half of the cooling duct 4 and a set of walls formed by a back wall 21 and four side walls 22a, 22b, 22c, 22d, and forming one half of the soundproofing housing 5.

The set of walls 20 has a general shape matched to the shape of one half of the motor 10, of the volute 12, of the nozzle 14 and of the stud 15. It thus defines:

- an upstream housing 25 (relative to the direction of air flow through the apparatus 1), of substantially semi-cylindrical shape, intended to accommodate a large portion of the body of the motor 10;
- a central housing 26 intended to accommodate the volute 12;
- a downstream housing 27 intended to accommodate the nozzle 14; and
- a housing 28 intended to accommodate the stud 15.

The upstream opening of the housing 25 is located away from the adjacent side wall 22a and comprises an air intake cowl so as to promote silent flow of the air therethrough.

The housing 26 is of semi-annular shape and is coaxial with the housing 25.

The housing 27 extends radially with respect to the housing 26 and communicates with a wall 30 forming a semi-tubular cavity, this cavity being intended to constitute, with the homologous portion 30 of the other half-casing 3, an opening for expelling the air from the casing 5, opening into the side wall 22b. The walls defining the housing 27 form a semi-annular cavity intended to accommodate a seal 31 made of soft material, for mounting this nozzle 14, for sealing and for damping the vibrations generated by the operation of the fan 2. The wall 30 also includes such a semi-annular cavity for accommodating a seal 32.

The housing 28 is provided diametrically opposite the housing 27, coaxially therewith, and is designed to accommodate the stud 15 with interposition of a seal 33 made of soft material, for mounting the fan 2 and for damping the vibrations generated by the operation thereof.

The assembly face of each of the two half-casings 3 lies in a plane passing substantially through the axis of the housings 25 to 28.

The side wall 22c located opposite the wall 22b with respect to the duct 4 has a semicircular recess 35 intended to constitute, with the homologous recess in the other half-casing 3, an inlet opening for air to enter the casing 5.

Furthermore, the side wall 22a has a semicircular wall 36 coaxial with the housing 25, intended to define, with the homologous semicircular wall of the other half-casing 3, a circular housing 37 for closely accommodating the seal 13.

In practice, the fan 2 is fitted in one of the half-casings 3 by fitting the seals 13, 31 and 33 in the respective housings 37, 27 and 28, and then the other half-casing 3 is assembled and fastened to the first half-casing 3 by fitting screws or the like, thus integrally forming the duct 4, the casing 5, the various housings for mounting the fan 2 and the air inlet and outlet openings.

The fan 2 may thus be mounted easily in the duct 4 and, once assembled, this fan 2 is kept perfectly in place in this duct 4, with the vibrations being damped. In this mounting position, the walls 20 extend close to the wall of the motor 10 and of the volute 12, thus providing a passage for the forced flow of air in the immediate proximity of this motor 10 and this volute 12, and therefore cooling them substantially. The fact that this duct 4 is formed as one and the same piece with the soundproofing housing 5 makes it possible, by forced convection, to discharge the heat generated by the motor 10.

The design of the apparatus 1 in the form of two half-casings 3 that can be fitted together also has the following advantages: the number of parts making up the apparatus is appreciably reduced; it results in greater ease of assembly, and therefore a shorter assembly time; and less material is needed to make the duct 4 for cooling the motor 10 and the soundproofing housing 5.

Furthermore, the provision of the half-casings 3 by molding increases the possibility of positioning the duct 4 in the casing 5 and of optimally integrating into the apparatus 1 an air inlet having a high acoustic attenuation and a minimized pressure drop.

The invention has been described above with reference to one embodiment provided by way of example. It goes without saying that the invention is not limited to this embodiment and that it includes all variations and modifications covered by the appended claims. In particular, the casing portions need not be "half-casings" that is to say that one of these portions may have a different thickness from that of the other portion; the casing portions may be shaped so that they can be assembled together in assembly planes other than that shown, for example the apparatus may comprise a left-hand casing portion and a right-hand casing portion that can be assembled together in an assembly plane perpendicular to that shown in the figures; the casing portions may also be shaped so as to be able to be assembled together in a plane perpendicular to the axis of the housings 25 and 26 of the duct 4, so that there would thus exist an upper casing portion and a lower casing portion.

The invention claimed is:

1. An apparatus (1) for delivering a gas, comprising:
a fan (2) comprising a motor (10), a vaned rotor (11) and a volute (12) containing the rotor (11), a motor-cooling duct (4) for cooling the motor, and a soundproofing housing (5) containing the fan (2) and the motor-cooling duct (4), wherein the motor-cooling duct (4) has a shape matched to a shape of the motor (10) and that of the volute (12) of the fan (2), so that walls (20) defining the motor-cooling duct (4) are spaced from a wall of the motor (10) and the volute (12), thus providing a flowing duct around the motor (10) and the volute (12); and
two casing portions (3), one of which includes a set of walls comprising a back wall (21) and at least one side wall (22a, 22b, 22c, 22d) forming a portion of the soundproofing housing (5), wherein a portion of the set of walls (20) defines the motor-cooling duct (4), and the other of said two casing portions includes a set of walls comprising a back wall (21) and at least one side wall (22a, 22b, 22c, 22d) forming a complementary portion of the soundproofing housing (5), wherein a complementary portion of the set of walls (20) defines the motor-cooling duct (4), said portions of the soundproofing housing (5) and of the motor-cooling duct (4) on the same casing portion (3) being integral with one another, and the two casing portions (3) being adapted to be assembled together around the fan (2) so as jointly to form said motor-cooling duct (4) and said soundproofing housing (5).

2. The apparatus as claimed in claim 1, wherein the two casing portions are half-casings (3) that are adapted to be assembled together in an assembly plane passing substantially through a longitudinal axis of the motor-cooling duct (4).

3. The apparatus as claimed in claim 1, wherein the two casing portions are adapted to be assembled together in an assembly plane substantially perpendicular to a longitudinal axis of the motor-cooling duct.

4. The apparatus as claimed in claim 1, wherein each of said two casing portions (3) forms at least one housing portion (25 to 28; 37) that jointly form, after assembly of the two casing portions (3), a housing adapted to accommodate a corresponding portion of the fan (2).

5. The apparatus as claimed in claim 4, wherein each of said two casing portions (3) comprises a portion for housing an outlet nozzle (14) of the volute (12), the two portions for housing the outlet nozzle (14) jointly forming, after assembly of the two casing portions, a further housing (27) adapted to accommodate the outlet nozzle (14) of the volute (12).

6. The apparatus as claimed in claim 4, wherein the housing (28) is adapted to accommodate a stud (15) for fitting the fan (2).

7. The apparatus as claimed in claim 6, wherein each said housing portion for fitting the fan (2) is provided at a location in the motor-cooling duct (4) diametrically opposed to an outlet nozzle (14) of the volute (12).

8. The apparatus as claimed in claim 1, wherein each of the two casing portions (3) comprises four side walls (22a, 22b, 22c, 22d).

9. The apparatus as claimed in claim 1, wherein the two casing portions are provided by molding.

10. The apparatus as claimed in claim 1, wherein the motor-cooling duct is formed from the same pieces as the soundproofing housing.

11. The apparatus as claimed in claim 1, wherein an internal wall of the motor-cooling duct (4) has a shape that matches an external contour of the motor (10) and of the volute (12) of the fan (2).

12. The apparatus as claimed in claim 1, wherein the two casing portions (3) are fastened together around the fan (2).

13. An apparatus (1) for delivering a gas, comprising:
a fan (2) comprising a motor (10), a vaned rotor (11) and a volute (12) containing the rotor (11), a motor-cooling duct (4) for cooling the motor, and a soundproofing housing (5) containing the fan (2) and the motor-cooling duct (4), wherein the motor-cooling duct (4) has a shape matched to a shape of the motor (10) and that of the volute (12) of the fan (2), so that walls (20) defining the motor-cooling duct (4) are spaced from a wall of the motor (10) and the volute (12), thus providing a flowing duct around the motor (10) and the volute (12); and
two casing portions (3), one of which includes a set of walls comprising a back wall (21) and at least one side wall (22a, 22b, 22c, 22d) forming a portion of the soundproofing housing (5), wherein a portion of the set of walls (20) defines the motor-cooling duct (4), and the other of said two casing portions includes a set of walls comprising a back wall (21) and at least one side wall (22a, 22b, 22c, 22d) forming a complementary portion of the soundproofing housing (5), wherein a complementary portion of the set of walls (20) defines the motor-cooling duct (4), said portions of the soundproofing housing (5) and of the motor-cooling duct (4) on the same casing portion (3) being integral with one another, and the two casing portions (3) being adapted to be assembled together around the fan (2) so as jointly to form said motor-cooling duct (4) and said soundproofing housing (5),
wherein each of said two casing portions (3) forms at least one housing portion (25 to 28; 37) that jointly form, after assembly of the two casing portions (3), a housing adapted to accommodate a corresponding portion of the fan (2), and wherein each of said two casing portions (3) comprises a lower housing portion that jointly form, after assembly of the casing portions (3), a further housing (37) adapted to accommodate an opposite end of the motor (10) from the volute (12) or a piece (13) fixed at the opposite end of the motor.

14. The apparatus as claimed in claim 13, wherein each of said two casing portions (3) comprises a portion for housing the outlet nozzle (14) of the volute (12), the two portions for housing the outlet nozzle (14) of the volute (12) jointly forming, after assembly of the casing portions, a yet further housing (27) adapted to accommodate the outlet nozzle (14) of the volute (12).

* * * * *